(12) United States Patent
Mamiya (10) Patent No.: US 9,820,724 B2
(45) Date of Patent: Nov. 21, 2017

(54) ENDOSCOPE PUNCTURE NEEDLE AND BIOPSY SYSTEM

(71) Applicant: OLYMPUS CORPORATION, Hachioji-shi, Tokyo (JP)

(72) Inventor: Tomohiko Mamiya, Kawasaki (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/372,252

(22) Filed: Dec. 7, 2016

(65) Prior Publication Data

US 2017/0079628 A1 Mar. 23, 2017

Related U.S. Application Data

(63) Continuation of application No. PCT/JP2015/083913, filed on Dec. 2, 2015.

(30) Foreign Application Priority Data

Mar. 6, 2015 (JP) .................................. 2015-044880

(51) Int. Cl.
| | |
|---|---|
| A61B 1/06 | (2006.01) |
| A61B 17/34 | (2006.01) |
| A61B 10/04 | (2006.01) |
| A61B 8/00 | (2006.01) |
| A61B 1/00 | (2006.01) |
| A61B 1/04 | (2006.01) |

(Continued)

(52) U.S. Cl.
CPC .......... *A61B 10/04* (2013.01); *A61B 1/00131* (2013.01); *A61B 1/018* (2013.01); *A61B 1/04* (2013.01); *A61B 1/06* (2013.01); *A61B 8/00* (2013.01); *A61B 8/12* (2013.01); *A61B 10/0233* (2013.01); *A61B 17/3478* (2013.01); *A61B 2010/045* (2013.01)

(58) Field of Classification Search
CPC . A61B 10/04; A61B 10/0233; A61B 1/00131; A61B 2010/045
See application file for complete search history.

(56) References Cited

U.S. PATENT DOCUMENTS

| | | | |
|---|---|---|---|
| 5,601,588 A | 2/1997 | Tonomura et al. | |
| 2011/0301413 A1 | 12/2011 | Morimoto | |

(Continued)

FOREIGN PATENT DOCUMENTS

| | | | |
|---|---|---|---|
| JP | H08-150145 A | 6/1996 | |
| JP | 2001-120557 A | 5/2001 | |

(Continued)

OTHER PUBLICATIONS

Feb. 2, 2016 International Search Report issued in International Patent Application No. PCT/JP2015/083913.

*Primary Examiner* — Sean Dougherty
(74) *Attorney, Agent, or Firm* — Oliff PLC (57) ABSTRACT

An endoscope puncture needle is provided with: an outer sheath; a needle tube arranged inside the outer sheath; an operation main body; a needle slider; an engaging mechanism; a proximal-end-side inner tube arranged at an inside of a proximal end of the outer sheath; and a distal-end-side inner tube arranged inside a distal end section of the outer sheath and has an inner circumferential surface that is relatively harder than the proximal-end-side inner tube. When the needle slider is engaged to the operation main body, a distal end of the needle tube is arranged inside the distal-end-side inner tube.

8 Claims, 8 Drawing Sheets

(51) Int. Cl.
*A61B 8/12* (2006.01)
*A61B 10/02* (2006.01)
*A61B 1/018* (2006.01)

(56) References Cited

U.S. PATENT DOCUMENTS

2012/0184818 A1 7/2012 Sugisawa et al.
2013/0184732 A1 7/2013 Tanaka et al.

FOREIGN PATENT DOCUMENTS

| JP | 2012-016576 A | 1/2012 |
| JP | 2012-161591 A | 8/2012 |
| JP | 2013-144012 A | 7/2013 |
| JP | 2013-172842 A | 9/2013 |

ENDOSCOPE PUNCTURE NEEDLE AND BIOPSY SYSTEM

The application is a continuation application based on PCT Patent Application No. PCT/JP2015/083913, filed Dec. 2, 2015, claiming priority is based on Japanese Patent Application No. 2015-044880, filed Mar. 6, 2015, the contents of which are incorporated herein by reference.

FIELD OF THE INVENTION

The present invention relates to an endoscope puncture needle and a biopsy system.

DESCRIPTION OF RELATED ART

In the related art, an inspection method which is referred to as a biopsy and includes collecting a small amount of body tissue and observing the body tissue using a microscope is known. In case of collecting tissue of the deep portion of an organ or the like, since an observation by using an optical endoscope is difficult, ultrasonic tomographic images of an organ are acquired by using an ultrasonic endoscope or the like, and tissue is collected by piercing a puncture needle having a tubular needle tube into the organ under ultrasonic observation in some cases.

For example, a puncture needle device in which an outer needle and an inner needle are arranged in a sheath that can be inserted into a treatment tool channel of an ultrasonic endoscope or the like is disclosed in Japanese Unexamined Patent Application, First Publication No. 2001-120557. Since the puncture needle device disclosed in Japanese Unexamined Patent Application, First Publication No. 2001-120557 is provided with the sheath, an inner surface of the treatment tool channel is not easily damaged by sharp distal ends of the outer needle and the inner needle.

A puncture needle that is used while being inserted into an endoscope is required to be able to be bent and deformed by the endoscope and to hardly buckle inside the endoscope. For example, a puncture needle device in which an outer cylindrical tube having excellent flexibility and an inner cylindrical tube that is harder than the outer cylindrical tube are installed substantially coaxially with each other and a puncture needle is inserted into the inner cylindrical tube is disclosed in Japanese Unexamined Patent Application, First Publication No. 2013-172842.

In the puncture needle device disclosed in Japanese Unexamined Patent Application, First Publication No. 2013-172842, it is disclosed that a main component of the outer cylindrical tube is polytetrafluoroethylene (PTFE), and a main component of the inner cylindrical tube is polyether ether ketone (PEEK).

SUMMARY OF THE INVENTION

An endoscope puncture needle according to a first aspect of the present invention includes: an outer sheath which is insertable into a channel of an endoscope; a needle tube having a needle tip and arranged inside the outer sheath; an operation main body connected to a proximal end of the outer sheath; a needle slider connected to a proximal end of the needle tube and is provided to be movable along a longitudinal axis of the operation main body with respect to the operation main body; an engaging mechanism in which the needle slider is engaged to the operation main body in a longitudinal axial direction of the operation main body; a proximal-end-side inner tube arranged at an inside of a proximal end of the outer sheath and made of plastics; and a distal-end-side inner tube arranged at an inside of a distal end section of the outer sheath, through which the needle tube is insertable, and made of plastics, the distal-end-side inner tube having an inner circumferential surface that is relatively harder than the proximal-end-side inner tube. A distal end of the needle tube is arranged inside the distal-end-side inner tube when the needle slider is engaged to the operation main body.

According to a second aspect of the present invention, in the endoscope puncture needle according to the first aspect may further include an attachment adapter which slidably supports the operation main body and is attachable to the endoscope. A distal end of the outer sheath may be arranged at more distal position than a proximal end of an active bending section when the attachment adapter is attached to the endoscope, the active bending section deforming the channel to a bent shape, and the distal-end-side inner tube may be arranged inside the outer sheath along a central line of the outer sheath in a range from the proximal end of the active bending section to the distal end of the outer sheath.

According to a third aspect of the present invention, in the endoscope puncture needle according to the first aspect, may further include an attachment adapter slidably supporting the operation main body and being attachable to the endoscope. A distal end of the outer sheath may be arranged at more distal position a proximal end of a raising base of the endoscope when the attachment adapter is attached to the endoscope, and the distal-end-side inner tube may be arranged inside the outer sheath along a central line of the outer sheath in a range from the proximal end of the raising base to the distal end of the outer sheath.

According to a fourth aspect of the present invention, in the endoscope puncture needle according to the first aspect, may further include an attachment adapter slidably supporting the operation main body and being attachable to the endoscope. A distal end of the outer sheath may be arranged at more distal position than a proximal end of a pipeline-shaped slope section being inclined with respect to a central axis of the channel of the endoscope when the attachment adapter is attached to the endoscope, and the distal-end-side inner tube may be arranged inside the outer sheath along a central line of the outer sheath in a range from the proximal end of the slope section to the distal end of the outer sheath.

According to a fifth aspect of the present invention, in the endoscope puncture needle according to the first aspect, may further include an attachment adapter slidably supporting the operation main body and being attachable to the endoscope. When the attachment adapter is attached to the endoscope, a distal end of the outer sheath may be located at more distal position than a proximal end of a raising base of the endoscope, and a proximal end of the distal-end-side inner tube may be located at more proximal position of the outer sheath than the proximal end of the raising base, and a distal end of the proximal-end-side inner tube may be located inside the outer sheath which is bent by an active bending section of the endoscope.

According to a sixth aspect of the present invention, in the endoscope puncture needle according to the first aspect, Shore hardness of an inner surface of the distal-end-side inner tube may be higher than Shore hardness of an inner surface of the proximal-end-side inner tube.

A biopsy system according to a seventh aspect of the present invention including: an endoscope provided with a channel through which a treatment tool is capable of being inserted and a bending application section by which the treatment tool in the channel is bent; and an endoscope puncture needle being attachable to the endoscope. The endoscope puncture needle includes: an outer sheath being insertable into a channel of an endoscope; a needle tube having a needle tip and arranged inside the outer sheath; an operation main body being connected to a proximal end of the outer sheath; a needle slider connected to a proximal end of the needle tube and is provided to be movable along a longitudinal axis of the operation main body with respect to the operation main body; an engaging mechanism in which the needle slider is engaged to the operation main body in a longitudinal axial direction of the operation main body; a proximal-end-side inner tube arranged at an inside of a proximal end section of the outer sheath and made of plastics; and a distal-end-side inner tube arranged at an inside of a distal end section of the outer sheath, through which the needle tube is insertable, and made of plastics, the distal-end-side inner tube having an inner circumferential surface that is relatively harder than the proximal-end-side inner tube. A distal end of the needle tube is arranged inside the distal-end-side inner tube when the needle slider is engaged to the operation main body.

An endoscope puncture needle according to a eighth aspect of the present invention includes: a sheath which is insertable into a channel of an endoscope; a needle tube having a needle tip and arranged inside the outer sheath; an operation main body connected to a proximal end of the outer sheath; a needle slider connected to a proximal end of the needle tube and is provided to be movable along a longitudinal axis of the operation main body with respect to the operation main body; and an engaging mechanism in which the needle slider is engaged to the operation main body in a longitudinal axial direction of the operation main body. The sheath has: a distal end region located at more distal position than a positon of the needle tip positioned inside the sheath in a state that the needle slider is engaged to the operation main body; and a proximal end region located at more proximal position than a positon of the needle tip in a state that the needle slider is engaged to the operation main body. An inner circumferential surface of the distal end region is relatively harder than an inner circumferential surface of the proximal end region.

Advantageous Effects of Invention

According to the endoscope puncture needle and the biopsy system according to the present invention, a needle tip is hardly punctured to an inner surface of a distal-end-side inner tube in a moving region of a distal end of a needle tube, and the needle tube and a sheath can be easily inserted into the channel even if a channel of an endoscope is bent.

DETAILED DESCRIPTION OF THE PREFERRED EMBODIMENTS

Figure 1:
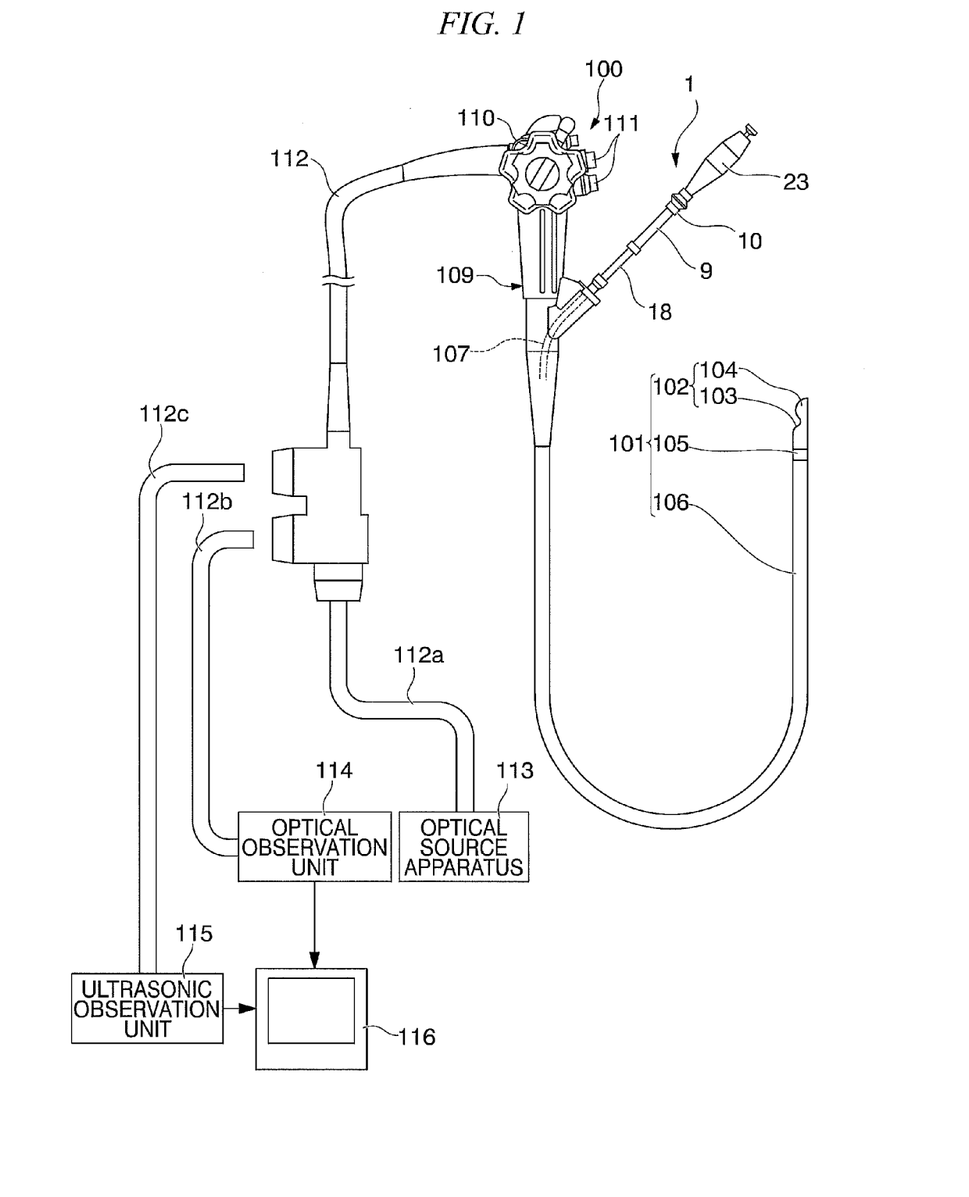
FIG. 1 is an overall diagram of a biopsy system provided with an endoscope puncture needle according to an embodiment of the present invention.
Figure 2:
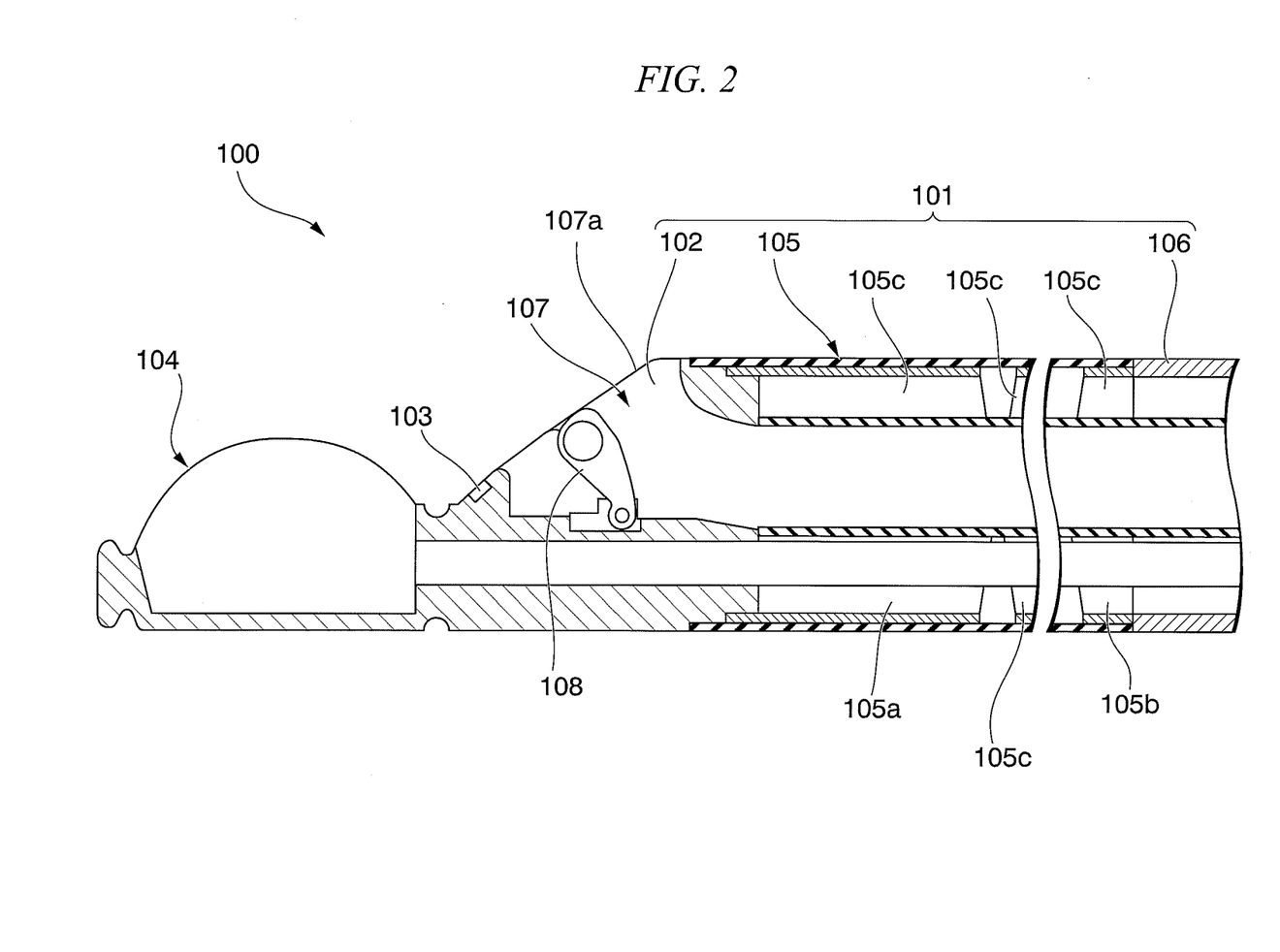
FIG. 2 is a cross-sectional view of a distal end portion of an ultrasonic endoscope in the biopsy system according to the embodiment of the present invention.
Figure 3:
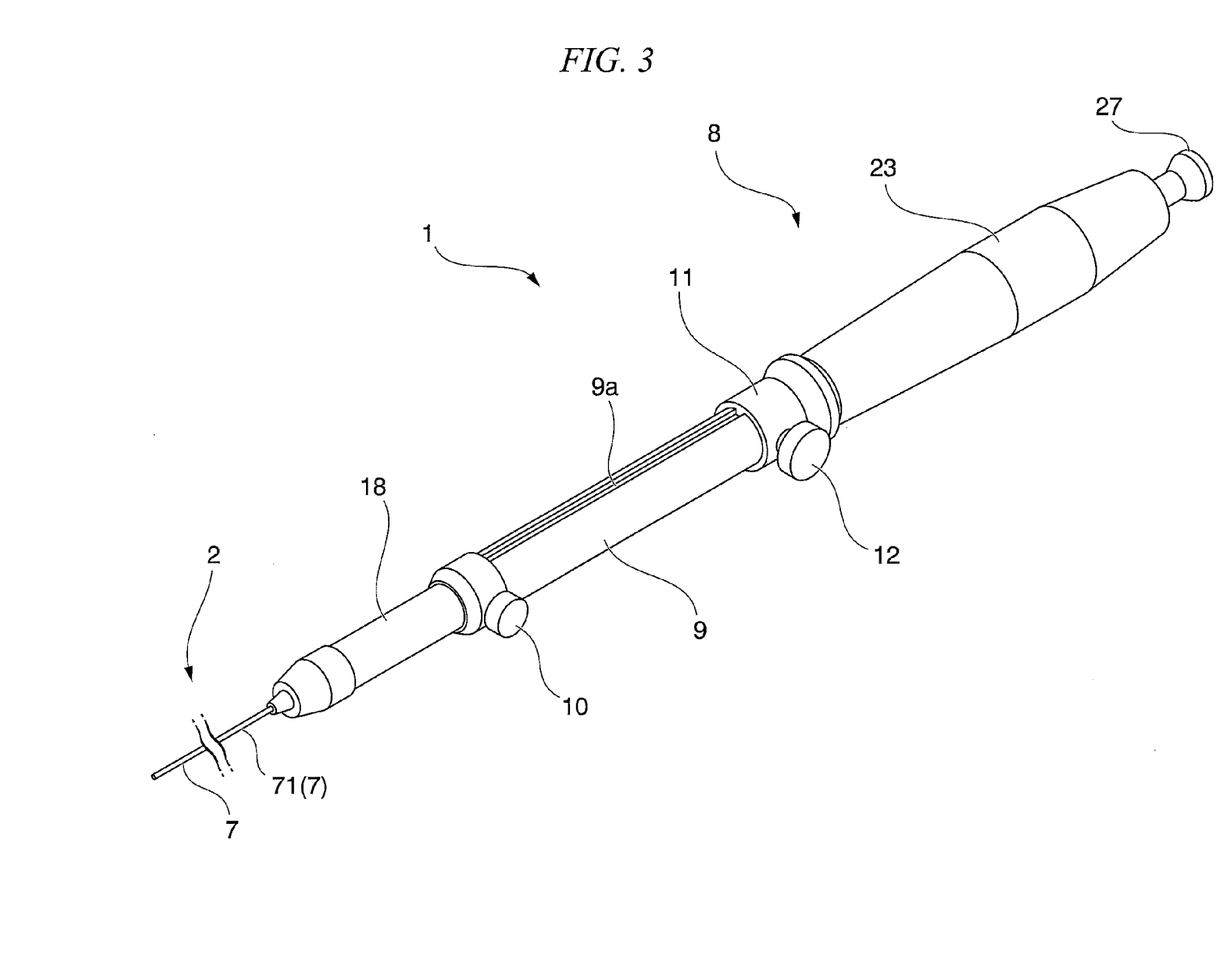
FIG. 3 is a perspective view of an endoscope puncture needle according to an embodiment of the present invention.
Figure 4:
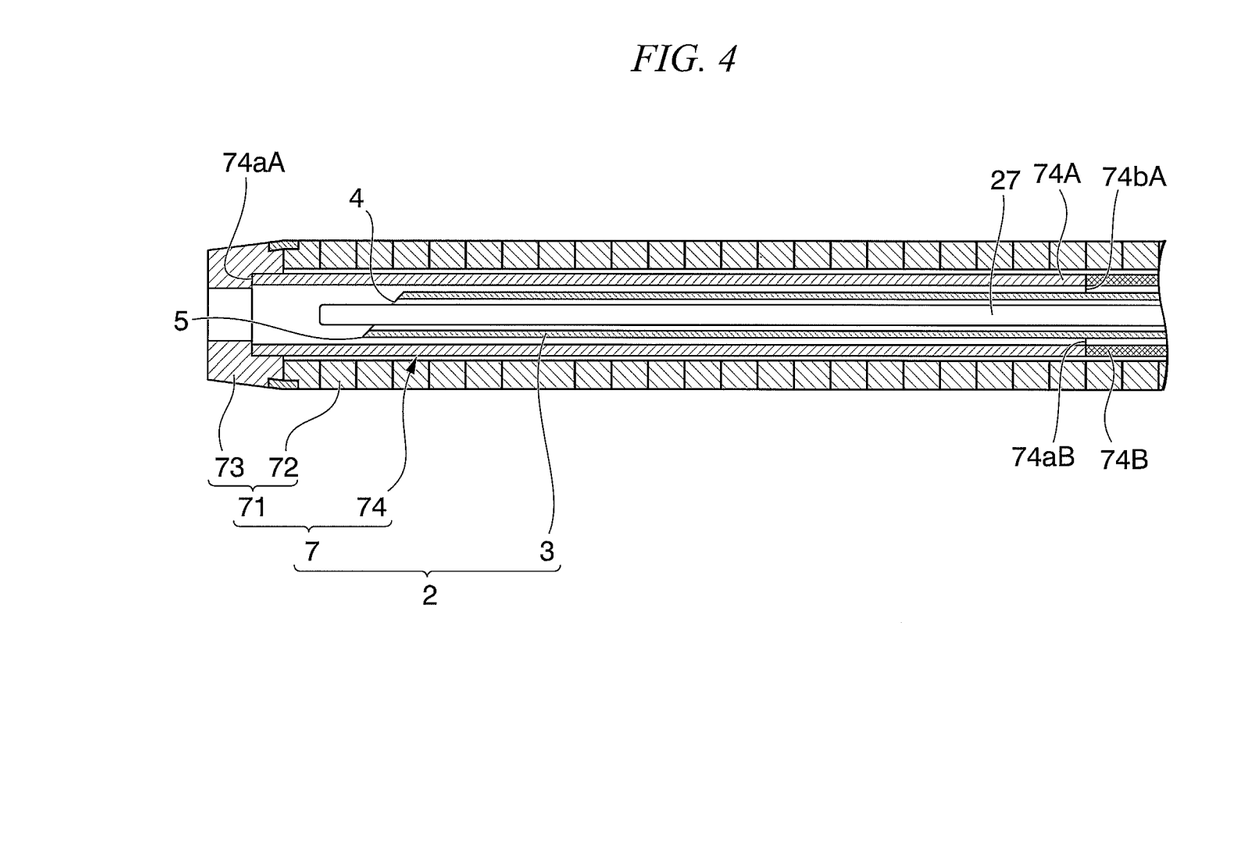
FIG. 4 is a cross-sectional view of a distal end portion of the endoscope puncture needle according to the embodiment of the present invention.
Figure 5:
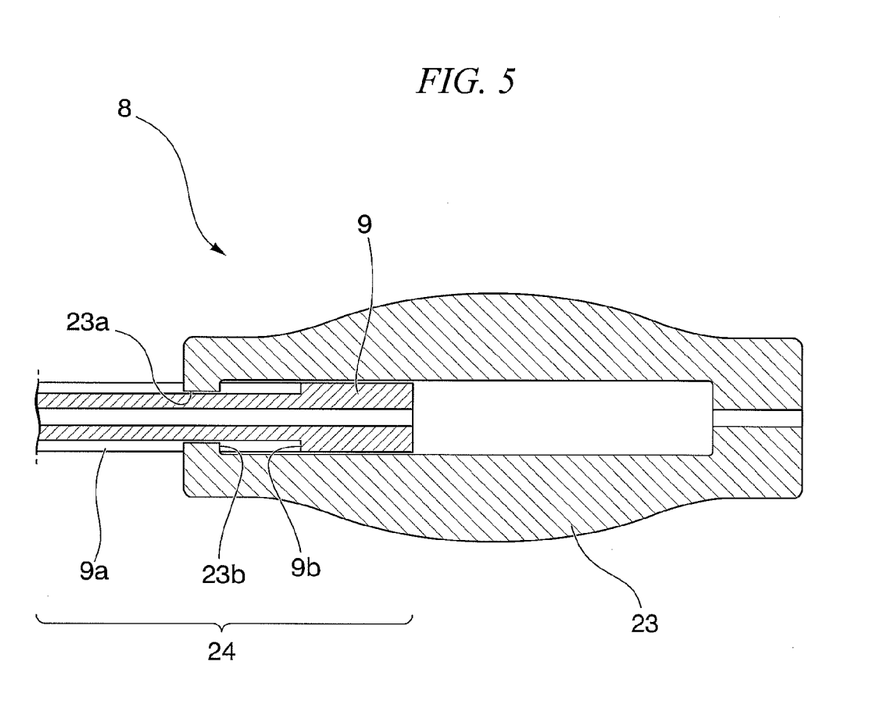
FIG. 5 is a schematic cross-sectional view of an operation section of the endoscope puncture needle according to the embodiment of the present invention.

An example of the present invention will be described, exemplifying a biopsy system provided with an endoscope puncture needle according to this embodiment. FIG. 1 is an overall diagram of a biopsy system provided with an endoscope puncture needle according to this embodiment. FIG. 2 is a cross-sectional view of a distal end portion of an ultrasonic endoscope in the biopsy system according to this embodiment. FIG. 3 is a perspective view of an endoscope puncture needle. FIG. 4 is a cross-sectional view of a distal end portion of the endoscope puncture needle. FIG. 5 is a schematic cross-sectional view of an operation section of the endoscope puncture needle.

A biopsy system 150 according to this embodiment shown in FIG. 1 is a medical instrument (a biopsy needle) capable of being used for a biopsy in which tissue in a body is collected. The biopsy system 150 is provided with an ultrasonic endoscope 100 and an endoscope puncture needle 1 (hereinafter simply referred to as a "puncture needle 1").

As shown in FIG. 1, the ultrasonic endoscope 100 is provided with an insertion section 101, an operation section 109, a universal cord 112, an optical source apparatus 113, an optical observation unit 114, and an ultrasonic observation unit 115. The insertion section 101 is inserted into a body from a distal end. The operation section 109 is attached to a proximal end of the insertion section 101. A first end of the universal cord 112 is connected to a lateral section of the operation section 109. A second end of the universal cord 112 is connected to the optical source apparatus 113 via a branching cable 112a, is connected to the optical observation unit 114 via a branching cable 112b, and is connected to the ultrasonic observation unit 115 via a branching cable 112c.

A distal end rigid section 102, an active bending section 105, and a flexible tube section 106 are provided at the insertion section 101 and are arranged in this order from a distal end side.

As shown in FIG. 2, the distal end rigid section 102 is provided with an optical imaging mechanism 103, an ultrasonic scanning mechanism 104, and a raising base 108. The optical imaging mechanism 103 is provided to perform optical observation. The ultrasonic scanning mechanism 104 is provided to perform ultrasonic observation. The raising base 108 is provided to adjust a direction of the puncture needle 1 inserted into a channel 107 which will be described below.

The optical imaging mechanism 103 is provided with an imaging optical system, an image sensor, and various constitutions (not shown) such as a central processing unit (CPU) which controls an operation of the image sensor. In the imaging optical system, a field of vision is directed diagonally in front of the distal end rigid section 102. The image sensor is constituted by a charge coupled device (CCD), a complementary metal oxide semiconductor (CMOS), or the like which detects an image of a subject which is incident through the imaging optical system.

The ultrasonic scanning mechanism (a probe) 104 is provided with an ultrasonic wave vibrator (not shown) which emits and receives ultrasonic waves. The ultrasonic scanning mechanism 104 receives reflected waves in which the ultrasonic waves emitted by the ultrasonic wave oscillator strikes an observed object and reflects by the ultrasonic wave oscillator, and outputs signals based on the ultrasonic waves received by the ultrasonic wave oscillator to the ultrasonic observation unit 115. The ultrasonic scanning mechanism 104 of this embodiment is used to acquire an ultrasonic image of tissue serving as a biopsy target and to acquire an ultrasonic image of a needle tube 3 in a process of a procedure of a biopsy.

As shown in FIG. 2, the raising base 108 is a member which changes a direction of a distal portion of a sheath section 7 (refer to FIG. 3) of the puncture needle 1 in a direction which intersects a central line of the insertion section 101. The raising base 108 presses an outer surface of the sheath section 7 by pulling a raising wire (not shown) extending to the operation section 109 at the operation section 109, and the sheath section 7 can thus be deformed in a bent state (refer to FIG. 6).

The active bending section 105 is a cylindrical member constituted of a plurality of joints 105c which are formed in a cylindrical shape and are arranged and coupled in a central line direction of the insertion section 101. The active bending section 105 is bent in a predetermined direction by pulling an angle wire (not shown), which is fixed to distal end 105a (refer to FIG. 2) of the active bending section 105 and extends to the operation section 109, at the operation section 109. The active bending section 105 of this embodiment can be bent in two directions in a scanning direction of ultrasonic waves of the ultrasonic scanning mechanism 104.

Both of the raising base 108 and the active bending section 105 are bending application sections which deform the puncture needle 1 serving as a treatment tool in this embodiment in accordance with an active bending operation using the operation section 109.

The flexible tube section 106 is a cylindrical member which is formed flexible so as to be able to guide the distal end rigid section 102 to a desired position in luminal tissue or coelom.

Conduits (not shown) for the purpose of air transfer, water transfer, suction, or the like with the channel 107 are provided inside the active bending section 105 and the flexible tube section 106.

As shown in FIGS. 1 and 2, the channel 107 is a cylindrical section through which the puncture needle 1 can be inserted.

As shown in FIG. 2, a distal end (a distal end opening 107a) of the channel 107 is opened at a portion near a distal end section of the distal end rigid section 102. As shown in FIG. 1, a proximal end of the channel 107 is opened at a lateral surface of a distal end side of the operation section 109. The raising base 108 can come into contact with the outer surface of the sheath section 7 of the puncture needle 1 in a process in which the sheath section 7 of the puncture needle 1 protrudes from the distal end of the channel 107. A proximal end port 107b which is formed in a flange shape is fixed to the proximal end of the channel 107. The puncture needle 1 which is used together with the ultrasonic endoscope 100 can be fixed to the proximal end port 107b.

As shown in FIG. 1, the operation section 109 has an outer surface formed such that an operator who uses the ultrasonic endoscope 100 can hold the operation section 109 in his/her hand. The operation section 109 is provided with a bending operation mechanism 110 and a plurality of switches 111. The bending operation mechanism 110 is provided to pull the angle wire to bend the active bending section 105 or pull the raising wire to operate the raising base 108. The plurality of switches 111 are provided to perform air transfer, water transfer, or suction via the pipelines.

The optical source apparatus 113 is a device which emits illumination light which is used by an optical imaging mechanism 103 to perform imaging.

The optical observation unit 114 is configured to display an image captured by an image sensor of the optical imaging mechanism 103 on a monitor 116.

The ultrasonic observation unit 115 receives a signal output from the ultrasonic scanning mechanism 104, generates an image on the basis of this signal, and displays the generated image on the monitor 116.

Next, a constitution of the puncture needle 1 according to this embodiment will be described.

As shown in FIG. 3, the puncture needle 1 is provided with an insertion body 2, an operation section 8, and a stylet 27.

The insertion body 2 is an elongated member capable of being inserted into the channel 107 of the ultrasonic endoscope 100 shown in FIG. 1. As shown in FIG. 4, the insertion body 2 is provided with the needle tube 3 and the sheath section 7.

The needle tube 3 is a cylindrical member which has distal and proximal ends and is advanced or retracted by the operation section 8 of the puncture needle 1.

A material which has flexibility and has elasticity which is easily restored to a rectilinear state even if the needle tube 3 is bent by an external force is preferably used as a material of the needle tube 3. For example, an alloy material such as a stainless steel alloy, a nickel titanium alloy, and a cobalt chromium alloy can be adopted as a material of the needle tube 3.

The distal end of the needle tube 3 is sharp enough for tissue to be punctured with the needle tube 3. The distal end of the needle tube 3 is provided with an opening 4 through which the tissue is suctioned inside the needle tube 3. A distal end of the opening 4 of the needle tube 3 is constituted as a needle tip 5 that is punctured to the tissue. A shape of the needle tip 5 is not particularly limited, but puncture performance with respect to the tissue is considered in the shape of the needle tip 5. The needle tip 5 of the needle tube 3 is disposed inside an outer sheath 71 which will be described below and can protrude from or withdraw into a distal end of the outer sheath 71.

The opening 4 provided at the distal end of the needle tube 3 is formed by cutting a distal end of a tubular member which forms the needle tube 3 at an oblique angle with respect to the tubular member itself and is formed to be sharp so as to be able to puncture to biological tissue. A specific shape of the opening 4 may be appropriately selected from various well-known shapes in consideration of tissue or the like serving as a target.

As shown in FIG. 4, the sheath section 7 is provided with the outer sheath 71 and an inner sheath 74.

The outer sheath 71 has a coil shape as a whole and can be inserted into the channel 107 of the ultrasonic endoscope 100.

The outer sheath 71 is provided with a coiled body 72 and a cylindrical distal end tip 73. The coiled body 72 is constituted by winding a metallic wire in a coil shape. The distal end tip 73 is fixed to a distal end of the coiled body 72.

A material and a shape of the wire which constitutes the coiled body 72 are appropriately selected focusing on easiness of bending and a recovering force of the coiled body 72. For example, the material of the wire is selected from stainless steel, a shape memory alloy, a super-elastic alloy, or the like, and the shape of the wire is selected from a circular cross-sectional shape, a rectangular cross-sectional shape, or the like.

The distal end tip 73 is a cylindrical member which is fixed to a distal end surface of the coiled body 72 and is formed with a through hole through which the needle tube 3 can be inserted.

The inner sheath 74 is provided with a distal-end-side inner tube 74A and a proximal-end-side inner tube 74B.

The distal-end-side inner tube 74A is a cylindrical member which has a distal end 74aA and a proximal end 74bA. The needle tube 3 slides inside the distal-end-side inner tube 74A. The distal-end-side inner tube 74A is made of a plastic for the purpose of reducing sliding resistance between the outer sheath 71 and the needle tube 3. The distal-end-side inner tube 74A is located between a distal end section of the outer sheath 71 and a distal end (a needle tip) of the needle tube 3 in a radial direction of the outer sheath 71 in a state in which a needle slider 23 is moved closest to a proximal end side along a longitudinal axis with respect to an operation main body 9, and the needle slider 23 is engaged to the operation main body 9 in a longitudinal axial direction of the operation main body 9. The distal-end-side inner tube 74A is configured such that a clearance between the outer sheath 71 and the needle tube 3 is reduced for preventing meandering of the needle tube 3. An inner surface of the distal-end-side inner tube 74A of this embodiment is harder than the proximal-end-side inner tube 74B to prevent the inner surface of the distal-end-side inner tube 74A from being damaged by the sharp distal end of the needle tube 3. The distal-end-side inner tube 74A may be a cylindrical member made of, for example, polyether ether ketone (PEEK). The proximal end 74bA of the distal-end-side inner tube 74A is located at more proximal position than a proximal end of a moving region of the distal end (the needle tip 5 in this embodiment) of the needle tube 3.

The distal end 74aA of the distal-end-side inner tube 74A is fixed to the distal end tip 73. In an entire length of the distal-end-side inner tube 74A, a proximal part located at more proximal position than a place at which the distal-end-side inner tube 74A is fixed to the distal end tip 73 is not fixed to the outer sheath 71. For this reason, the distal-end-side inner tube 74A can be relatively moved with respect to the outer sheath 71 when the outer sheath 71 and the distal-end-side inner tube 74A are bent.

The distal end 74aA of the distal-end-side inner tube 74A may be directly fixed to the coiled body 72 without being fixed to the distal end tip 73. The proximal end 74bA of the distal-end-side inner tube 74A may be connected to a distal end 74aB of the proximal-end-side inner tube 74B such that the distal end 74aA of the distal-end-side inner tube 74A is not fixed to the coiled body 72. In this case, the proximal-end-side inner tube 74B which will be described below is fixed to the coiled body 72 or the operation section 8 which will be described below (preferably the operation main body 9).

An inner diameter of the distal end tip 73 may be greater than an inner diameter of the inner sheath 74. When the inner diameter of the distal end tip 73 is greater than the inner diameter of the inner sheath 74, the needle tube 3 arranged in the inner sheath 74 is spaced apart from an inner surface of the distal end tip 73 at a position of the distal end tip 73, thereby frictional resistance is reduced compared to when the needle tube 3 slides with respect to the inner surface of the distal end tip 73.

Here, at the point of use, the moving region of the needle tip 5 may vary by receiving effects by expansion and contraction, a meandering state, or the like when the outer sheath 71, the inner sheath 74, and the needle tube 3 are used. The moving region of the distal end (the needle tip 5) of the needle tube 3 is limited by the operation section 8 in this embodiment. To be specific, the needle slider 23 shown in FIG. 3 is provided to be movable along the longitudinal axis of the operation main body 9 with respect to the operation main body 9. As shown in FIG. 5, the operation main body 9 slidably supports the needle slider 23 in a state in which a convex section 23a of the needle slider 23 is fitted into a concave section 9a of the operation main body 9 such that the needle slider 23 can be moved in an axial direction of the operation main body 9.

The needle slider 23 can be moved to a position which comes into contact with a stopper 11 (refer to FIG. 3) when the needle slider 23 is moved toward a distal end of the operation main body 9. The stopper 11 can be moved with respect to the operation main body 9 until the stopper 11 comes into contact with a portion (no reference numeral) of a distal end of the operation main body 9 whose diameter is enlarged. For this reason, the needle slider 23 is configured to be able to advance to a position at which the distal end of the needle tube 3 sufficiently protrudes from a distal end of the sheath section 7 when the stopper 11 comes into contact with the portion of the operation main body 9 whose diameter is enlarged.

As shown in FIG. 5, the operation section 8 is provided with an engaging mechanism 24 which restricts movement of the needle slider 23 toward a proximal side of the operation main body 9. The engaging mechanism 24 is constituted by an engaging surface 9b formed on the operation main body 9 and a contact surface 23b formed on the convex section 23a of the needle slider 23. The engaging surface 9b and the contact surface 23b come into contact with each other when the needle slider 23 is moved closest to the proximal end side along the longitudinal axis of the operation main body 9 with respect to the operation main body 9.

The needle slider 23 is engaged to the operation main body 9 in the longitudinal axial direction of the operation main body 9 in a state in which the engaging surface 9b and the contact surface 23b come into contact with each other. The needle slider 23 can be moved to a position which is engaged by the engaging mechanism 24 shown in FIG. 5 (a position at which the contact surface 23b of the convex section 23a comes into contact with the engaging surface 9b of the operation main body 9) when the needle slider 23 is moved toward the proximal end of the operation main body 9. When the needle slider 23 is engaged to the operation main body 9 by the engaging mechanism 24, the distal end of the needle tube 3 enters the distal-end-side inner tube 74A from the proximal end 74bA of the distal-end-side inner tube 74A and is disposed inside the distal-end-side inner tube 74A.

In other words, the needle slider 23 can be moved from a position at which the needle slider 23 is engaged to the operation main body 9 to a position at which the needle slider 23 comes into contact with the stopper 11 which is in contact with the portion of the operation main body 9 whose diameter is enlarged, and the distal end of the needle tube 3 can thus protrude from or withdraw into the distal end of the sheath section 7 in a process in which the needle slider 23 is moved between the two positions.

The proximal-end-side inner tube 74B is a cylindrical member which has the distal end 74*a*B and a proximal end (not shown). The proximal-end-side inner tube 74B is arranged inside the outer sheath 71. Part of the needle tube 3 other than the needle tip 5 (that is, a part of a distal portion of the needle tube 3 which is located at more proximal position than the needle tip 5) is inserted into the proximal-end-side inner tube 74B. In other words, the proximal-end-side inner tube 74B is arranged between a proximal end of the outer sheath 71 and a proximal end of the needle tube 3 in the radial direction of the outer sheath 71. The distal end 74*a*B of the proximal-end-side inner tube 74B is located at more proximal position than the moving region of the distal end (the needle tip 5) of the needle tube 3. The distal end 74*a*B of the proximal-end-side inner tube 74B is arranged substantially coaxially with the proximal end 74*b*A of the distal-end-side inner tube 74A.

In this embodiment, the proximal-end-side inner tube 74B is arranged at an inside of the outer sheath 71 where is more proximal side than the proximal end 74*b*A of the distal-end-side inner tube 74A such that the needle tip 5 does not come into contact with an inner surface of the proximal-end-side inner tube 74B. A proximal end (not shown) of the proximal-end-side inner tube 74B is fixed to the operation section 8.

The proximal end of the proximal-end-side inner tube 74B may not be directly fixed to the operation section 8. For example, the proximal-end-side inner tube 74B may be fixed to the outer sheath 71, and the operation section 8 may be fixed to the proximal end of the outer sheath 71.

The proximal-end-side inner tube 74B may be fixed to the needle tube 3. In this case, a gap corresponding to an amount of protrusion of the needle tube 3 from the outer sheath 71 is preferably provided between the distal end 74*a*B of the proximal-end-side inner tube 74B and the proximal end 74*b*A of the distal-end-side inner tube 74A. With such a constitution, since the needle tube 3 can protrude from the outer sheath 71 without a distal end side of the proximal-end-side inner tube 74B entering the distal-end-side inner tube 74A, the sheath section 7 is not necessary to increase an outer diameter.

In the proximal-end-side inner tube 74B, the meandering of the needle tube 3 is prevented by reducing the clearance between the outer sheath 71 and the needle tube 3. Since the proximal-end-side inner tube 74B is arranged in a region with which the sharp needle tip 5 of the needle tube 3 does not come in contact, it is not necessary to always select a material for the purpose of protection from the needle tip 5 of the needle tube 3. The proximal-end-side inner tube 74B may be made of a plastic. The proximal-end-side inner tube 74B may be a cylindrical member made of, for example, high density polyethylene (HDPE) to decrease sliding resistance with respect to the outer sheath 71 and the needle tube 3.

In a relationship between a constitution of the distal-end-side inner tube 74A and a constitution of the proximal-end-side inner tube 74B, constitutions of inner surfaces thereof satisfy at least one of the following (Condition 1) to (Condition 3).

(Condition 1)

The distal-end-side inner tube 74A and the proximal-end-side inner tube 74B are made of different materials, and the inner surface (an inner circumferential surface) of the distal-end-side inner tube 74A is harder than the inner surface (an inner circumferential surface) of the proximal-end-side inner tube 74B.

(Condition 2)

Materials of the distal-end-side inner tube 74A and the proximal-end-side inner tube 74B are not particularly limited, but a coating harder than the inner surface (the inner circumferential surface) of the proximal-end-side inner tube 74B is formed on the inner surface (the inner circumferential surface) of the distal-end-side inner tube 74A.

(Condition 3)

The distal-end-side inner tube 74A is a multilayer tube which has an outer circumferential section and an inner circumferential section, and a layer which is at an innermost circumference has the harder inner surface (inner circumferential surface) than the inner surface (the inner circumferential surface) of the proximal-end-side inner tube 74B.

In addition, a relationship between hardness of the inner surface of the distal-end-side inner tube 74A and hardness of the inner surface of the proximal-end-side inner tube 74B may be defined by Shore hardness (HS) of inner surfaces of each of the distal-end-side inner tube 74A and the proximal-end-side inner tube 74B. To be specific, Shore hardness of the inner surface of the distal-end-side inner tube 74A is higher than Shore hardness of the inner surface of the proximal-end-side inner tube 74B.

For example, the distal-end-side inner tube 74A may be made of a plastic whose Shore hardness is within a range of 84 or more and 107 or less such that the needle tip 5 is hardly punctured. In this case, the proximal-end-side inner tube 74B may have a softer constitution than the distal-end-side inner tube 74A and may be made of a plastic whose Shore hardness is within a range of 41 or more and 70 or less. To be specific, the distal-end-side inner tube 74A may be made of polyether ether ketone (PEEK). In this case, the proximal-end-side inner tube 74B may be made of polyethylene (PE).

As shown in FIGS. 1 and 3, the operation section 8 is connected to the proximal end of the outer sheath 71.

The operation section 8 is provided with the operation main body 9, an attachment adapter 18, and the needle slider 23. The attachment adapter 18 is provided at the distal end side of the operation main body 9. The needle slider 23 is provided at the proximal end side of the operation main body 9.

The operation main body 9 is formed of, for example, acrylonitrile butadiene styrene (ABS) or the like. The operation main body 9 has a lumen through which the needle tube 3 and the sheath section 7 are inserted. The distal end side of the operation main body 9 is inserted into the attachment adapter 18 which is formed in a tubular shape. The proximal end side of the operation main body 9 is inserted into the needle slider 23 which is formed in a tubular shape. The operation main body 9 and the attachment adapter 18, and the operation main body 9 and the needle slider 23 can slide in an axial direction while relative rotation thereof around an axis is suppressed by engaging grooves and convex sections or the like (not shown) which are formed in the outer circumferential surface thereof with each other. The outer sheath 71 of the sheath section 7 is connected to the operation main body 9. The sheath section 7 arranged inside the operation main body 9 is fixed to the operation main body 9.

The attachment adapter 18 is a cylindrical member which fixes the operation section 8 to the proximal end port 107*b* of the ultrasonic endoscope 100. The sheath section 7, the needle tube 3, and the stylet 27 are inserted into the attachment adapter 18.

The attachment adapter 18 is coupled to the operation main body 9 to be substantially coaxial with the operation main body 9.

The attachment adapter 18 and the operation main body 9 can be fixed by a fixing screw 10. When the fixing screw 10 is tightened to the operation main body 9, the attachment adapter 18 is pressed to the operation main body 9 so that the attachment adapter 18 and the operation main body 9 can be fixed without sliding to each other. The operation main body 9 can be moved with respect to the attachment adapter 18 along a central line of the attachment adapter 18 while the fixing screw 10 is loose. The operation section 8 is constituted such that the sheath section 7 is advanced together with the needle tube 3 when the operation main body 9 is moved toward a distal end side of the attachment adapter 18 with respect to the attachment adapter 18. Thus, a protruding length of the sheath section 7 from the channel 107 in a state that the operation section 8 is fixed to the ultrasonic endoscope 100 can be adjusted by changing a positional relationship between the attachment adapter 18 and the operation main body 9, and the protruding length can be fixed by the fixing screw 10.

Unevenness may be formed at an outer circumferential surface of a distal end section of the attachment adapter 18 such that the operator is capable of easily gripping the attachment adapter 18.

As shown in FIG. 3, the needle slider 23 is a cylindrical member which holds a proximal end portion of the needle tube 3. The proximal end side of the needle tube 3 protrudes from a proximal end of the sheath section 7, extends to an inside of the needle slider 23, and is connected to the needle slider 23 at a proximal end of the needle slider 23. In this embodiment, for example, the proximal end side of the needle tube 3 is fixed to the needle slider 23. The needle slider 23 is coupled to the operation main body 9 so as to be capable of moving with respect to the operation main body 9. The operation section 8 can advance the needle tube 3 with respect to the outer sheath 71 by moving the needle slider 23 toward the distal end side of the operation main body 9 with respect to the operation main body 9. As described above, the operation section 8 can advance or retract the needle tube 3 with respect to the outer sheath 71.

Unevenness may be formed at an outer circumferential surface of a distal end section of the needle slider 23 such that the operator is capable of easily gripping the attachment adapter 18.

As shown in FIG. 3, the stopper 11 is attached to the distal end side of the needle slider 23 so as to be capable of moving with respect to the operation main body 9. The stopper 11 has a fixing screw 12 and can be fixed to the operation main body 9 by tightening the fixing screw 12. Since the needle slider 23 can advance with respect to the operation main body 9 until the needle slider 23 comes into contact with the stopper 11, a maximum protruding length of the needle tube 3 from the sheath section 7 can be adjusted by adjusting a fixed position of the stopper 11 with respect to the operation main body 9.

A state that the needle slider 23 is at a position at which the needle slider 23 is moved to a limit at the proximal end side of the operation main body 9 is an initial state before the puncture needle 1 is used. In the initial state, the distal end (the needle tip 5) of the needle tube 3 is located inside the distal-end-side inner tube 74A.

As described above, in this embodiment, the operation section 8 defines the moving region of the distal end of the needle tube 3.

The stylet 27 is attached to a proximal end portion of the needle slider 23. The stylet 27 is a needle-shaped member which is inserted into the needle tube 3. A distal end of the stylet 27 is not limited to the needle shape, but may have an end surface along a surface which intersects a longitudinal axis of the stylet 27, and may have a curved surface such as a hemispherical surface.

Figure 6:
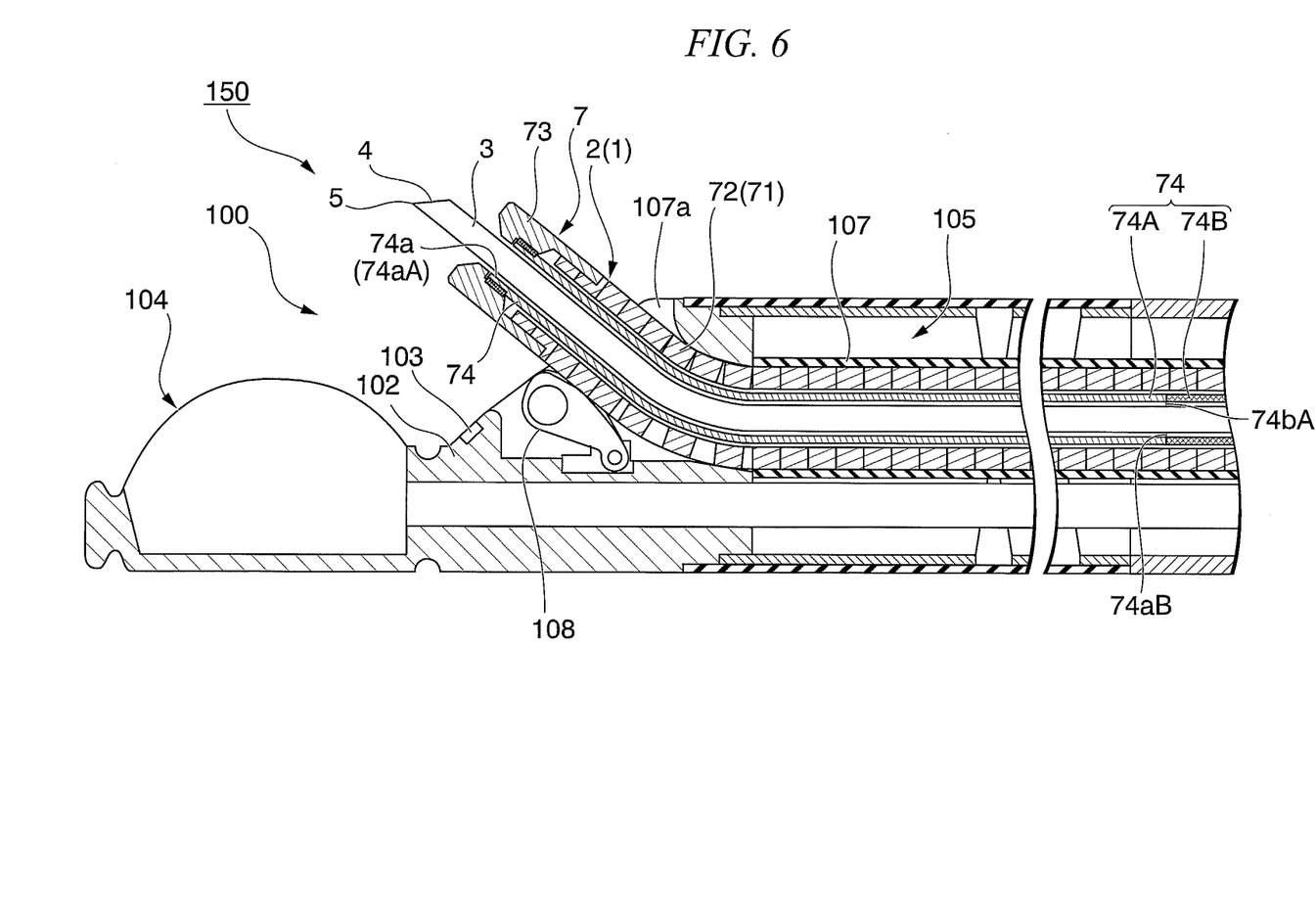
FIG. 6 is a view for describing an action of the endoscope puncture needle according to the embodiment of the present invention.

Next, an action of the biopsy system 150 according to this embodiment will be described. FIG. 6 is a view for describing an action of the puncture needle 1.

In the biopsy system 150 (refer to FIG. 1) according to this embodiment, as shown in FIGS. 4 and 6, the puncture needle 1 is moved inside the outer sheath 71 such that the needle tube 3 comes into contact with an inner surface of the inner sheath 74 rather than an inner surface of the coiled body 72 of the outer sheath 71. In particular, the needle tip 5 of the needle tube 3 advances or retracts in the distal-end-side inner tube 74A and can protrude from an opening of a distal end of the distal-end-side inner tube 74A.

Since the inner sheath 74 is made of a plastic, frictional resistance between the needle tube 3 and the inner sheath 74 is smaller than frictional resistance between metals. For this reason, in this embodiment, a smaller amount of force than a conventional puncture needle is required for moving the needle tube 3 with respect to the sheath section 7.

When the sheath section 7 is located at the active bending section 105 and the raising base 108 of the ultrasonic endoscope 100, the sheath section 7 is deformed in a bent shape by the active bending section 105 and the raising base 108 (refer to FIG. 6). When the sheath section 7 is in the bent shape, an inclined angle of the needle tip 5 with respect to an inner surface of the sheath section 7 is greater than that when the sheath section 7 is in a rectilinear state. For this reason, when the sheath section 7 is in the bent state, the sheath section 7 and the needle tip 5 have a positional relationship in which the needle tip 5 easily punctures the inner surface of the sheath section 7 in comparison with the sheath section 7 which is in the rectilinear state. However, since the inner surface of the distal-end-side inner tube 74A of this embodiment is a hard surface so as to hardly puncture the needle tip 5, the needle tip 5 hardly punctures the distal-end-side inner tube 74A even if the needle tip 5 is moved in the distal-end-side inner tube 74A.

When the sheath section 7 is located at the active bending section 105 and the raising base 108 of the ultrasonic endoscope 100, the needle tube 3 passing through the sheath section 7 which is in the bent state is difficult to move at a part of the sheath section 7 which is bent and deformed due to a magnitude of frictional resistance with respect to the sheath section 7 in comparison with the sheath section 7 which is in the rectilinear state. In the sheath section 7 of the puncture needle 1 provided in the biopsy system 150 according to this embodiment, the plastic inner sheath 74 is arranged inside the metallic coiled body 72. For this reason, an amount of force required for moving the needle tube 3 at a portion at which frictional resistance is great due to bent and deformation of the sheath section 7 is smaller than that when there is no inner sheath 74. In other words, according to the puncture needle 1 according to this embodiment, the needle tube 3 can be moved as intended by the operator with a light force even if the sheath section 7 is bent and deformed.

Unlike the distal-end-side inner tube 74A, since the proximal-end-side inner tube 74B is not always necessary to consider the inner surface which is difficult to puncture the needle tip 5, a more flexible tube than the distal-end-side inner tube 74A may be adopted. For this reason, the insertion body 2 can be smoothly inserted in a process in which the insertion body 2 is inserted into the channel 107 having a complicated bent shape when the flexible tube section 106 of the ultrasonic endoscope 100 is in the body and meanders or the like.

In this embodiment, since the frictional resistance between the plastic inner sheath 74 and the metallic needle tube 3 is small, an amount of force for moving the needle tube 3 with respect to the sheath section 7 is small enough even if a difference (a clearance) between the inner diameter of the inner sheath 74 and the outer diameter of the needle tube 3 is small. For this reason, a gap in which the needle tube 3 is likely to meander in the sheath section 7 can be reduced, and following performance of the distal end portion of the needle tube 3 with respect to the advancing and retracting operation of the needle tube 3 in the operation section 8 is good.

In a conventional puncture needle, a distal end of a needle tube is not moved even if a proximal end portion of the needle tube is press toward the distal end thereof by a slider, and the slider is pushed back toward the proximal end with a recovering force by which the meandering needle tube is returned in a rectilinear shape. However, in this embodiment, since the needle tube 3 does not easily meander in the sheath section 7, when the needle tube 3 is moved toward the distal end by using the needle slider 23 of the operation section 8, the meandering of the needle tube 3 does not easily accumulate in the sheath section 7 and thus the distal end of the needle tube 3 is efficiently performed. As a result, in the biopsy system 150 according to this embodiment, as described above, the slider is not easily pushed back toward the proximal end with the recovering force by which the needle tube is returned in the rectilinear shape.

In this embodiment, the distal end 74aA of the distal-end-side inner tube 74A is fixed to the distal end tip 73, and the distal end tip 73 is further fixed to a distal end section of the coiled body 72. For this reason, the distal end tip 73 of the distal end portion of the outer sheath 71 holds the distal-end-side inner tube 74A such that a distal end portion of the inner sheath 74 is not moved inside the coiled body 72 even if the sheath section 7 is deformed in the bent shape, or an amount of operation force is transferred from the proximal end side of the sheath section 7 to the distal end side of the sheath section 7. Thus, since the distal end of the inner sheath 74 is not moved more proximal side than the distal end of the outer sheath 71, the coiled body 72 of the outer sheath 71 does not come into direct contact with the needle tube 3.

The distal end 74aA of the distal-end-side inner tube 74A is fixed to the distal end section of the coiled body 72 via the distal end tip 73, and a portion of the distal-end-side inner tube 74A which is more proximal side than the distal end 74aA of the distal-end-side inner tube 74A is slidable with respect to the coiled body 72. For this reason, extending of the coiled body 72 is not regulated even if the distal-end-side inner tube 74A is arranged in the coiled body 72. Thus, flexibility of the outer sheath 71 constituting the coiled body 72 is not easily reduced.

In this embodiment, the distal end tip 73 is not necessary to always arrange at the distal end portion of the outer sheath 71, and a distal end 74a of the inner sheath 74 may be directly fixed to the distal end portion of the coiled body 72 of the outer sheath 71.

In this embodiment, in the coiled body 72 of the outer sheath 71, a gap is generated in the wire constituting the coiled body 72 while the outer sheath 71 is bent by the raising base 108 and the active bending section 105. When the distal end of the needle tube 3 enters and is caught by the gap of the wire, the moving of the needle tube 3 is likely to be obstructed, or the distal end of the needle tube 3 is likely to be deformed. In this embodiment, since the inner sheath 74 is arranged inside of the coiled body 72 of the outer sheath 71, the gap of the wire of the coiled body 72 is covered with the inner sheath 74. As a result, the needle tube 3 advancing or retracting inside the inner sheath 74 is not easily caught by the gap of the wire of the coiled body 72 even if the insertion body 2 is bent at a position of the raising base 108 or the active bending section 105. When a plastic structure which covers the wire having a gap at an inner wall of a portion of the outer sheath 71 bent in a bent shape whose curvature radius is great is provided, the catching of the distal end of the needle tube 3 can be prevented even if an entire area of the coiled body 72 is not covered.

Figure 7:
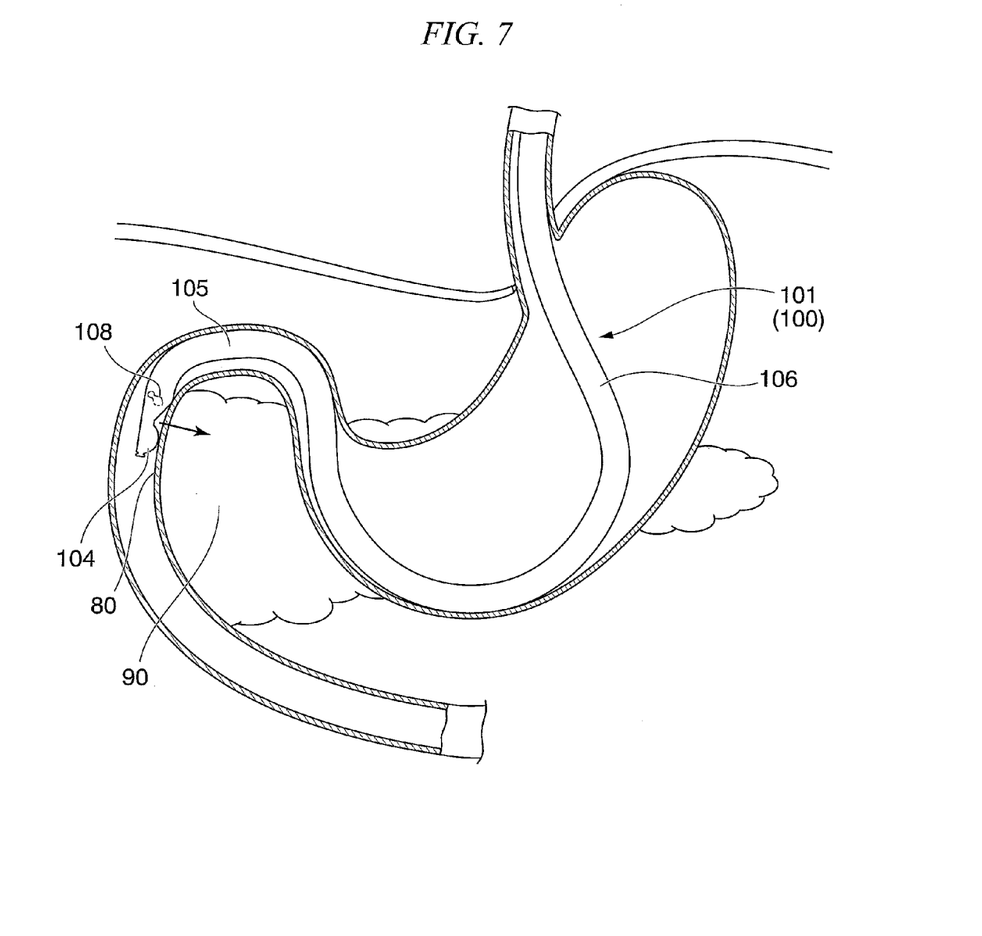
FIG. 7 is a schematic diagram illustrating a process of an example of a procedure of a biopsy using the endoscope puncture needle according to the embodiment of the present invention.
Figure 8:
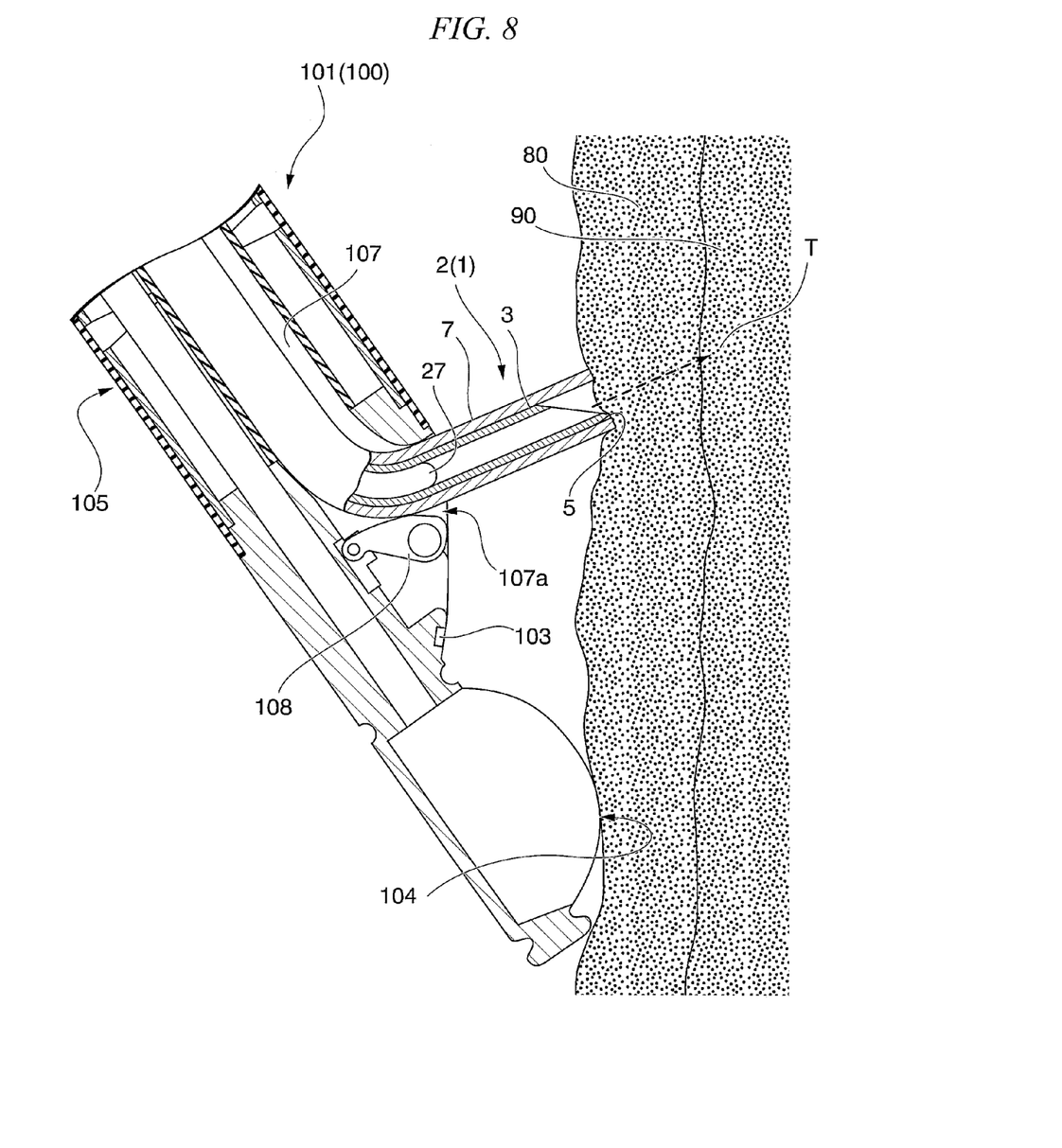
FIG. 8 is a schematic diagram illustrating a process of puncturing a needle tube to a tissue in an example of a procedure of a biopsy by using an endoscope puncture needle according to an embodiment of the present invention.

An example of a procedure using the puncture needle 1 according to this embodiment will be illustrated. FIG. 7 is a schematic diagram illustrating a process of the example of the procedure of a biopsy using the puncture needle according to this embodiment. FIG. 8 is a schematic diagram illustrating a process of puncturing tissue using a needle tube in the example of the procedure using the puncture needle according to this embodiment.

Hereinafter, a usage aspect of the puncture needle 1 will be described, exemplifying treatment of the biopsy in which the needle tube 3 of the puncture needle 1 punctures lesions in the body serving as target tissue and cells or the like of the lesions are collected through the inside of the needle tube 3. The procedure of the biopsy which will be exemplified below is an example of the biopsy with respect to a pancreatic head in pancreas 90 shown in FIGS. 7 and 8. An adaptable target of the puncture needle 1 according to this embodiment is not limited to the puncturing in the biopsy of the pancreatic head.

First, the operator inserts the insertion section 101 of the ultrasonic endoscope 100 shown in FIG. 1 into the body, introduces a distal end section of the insertion section 101 into a portion near the target tissue (the pancreatic head in this embodiment) while appropriately bending the active bending section 105 under observation by using the optical imaging mechanism 103. After the introducing, the operator determines a site on which the biopsy is performed on the basis of observed results by the optical imaging mechanism 103 and the ultrasonic scanning mechanism 104. For example, when the biopsy is performed on the pancreatic head, the insertion section 101 is moved while the active bending section 105 is bent such that the optical imaging mechanism 103 and the ultrasonic scanning mechanism 104 which are provided at the insertion section 101 of the ultrasonic endoscope 100 reach the duodenum 80.

When the biopsy on the pancreatic head is performed by using the ultrasonic endoscope 100, there is a need to bend the active bending section 105 to capture a puncturing site of the puncture needle 1 in a field of vision of the ultrasonic endoscope 100. In particular, when the biopsy on the pancreatic head is performed as in this embodiment, the active bending section 105 is bent to an extent close to a performance limit of the active bending section 105 of the ultrasonic endoscope 100.

Next, the operator inserts the distal end side of the insertion body 2 of the puncture needle 1 into the channel 107 from the proximal end port 107b provided at the operation section 109 of the ultrasonic endoscope 100 shown in FIG. 1. The operator couples the attachment adapter 18 of the operation section 109 to the proximal end port 107b. Thus, the operation section 8 of the puncture needle 1 is fixed to the ultrasonic endoscope 100 so as not to rotate with respect to the operation section 109.

For example, when back cutting is performed on the needle tube 3, the needle tip 5 is difficult to come into contact with the inner surface of the sheath section 7. In addition, similarly, when the needle tube 3 is, for example, a Menghini needle, the needle tip 5 is difficult to come into contact with the inner surface of the sheath section 7.

Next, the operator loosens the fixing screw 10 (refer to FIG. 3), and adjusts an amount of protrusion of the sheath section 7 from a distal end of the insertion section 101 of the ultrasonic endoscope 100 to an appropriate amount by relatively sliding the attachment adapter 18 and the operation main body 9 while observing the sheath section 7 and the inside of the body by the optical imaging mechanism 103 and the ultrasonic scanning mechanism 104. After the adjusting, the operator tightens the fixing screw 10 to fix the amount of protrusion.

Next, the stopper 11 is moved in consideration of a distance from target tissue T on which the biopsy is performed on the basis of the observed results using the ultrasonic scanning mechanism 104 and is fixed to the operation main body 9 at a desired position, and a maximum protruding length of the needle tube 3 is adjusted.

As shown in FIG. 8, a protruding direction of the insertion body 2 from the distal end opening 107*a* of the channel 107 is set by using the raising base 108 such that the needle tube 3 is pushed toward a position of the target tissue T.

The raising base 108 presses the outer surface of the sheath section 7, thus the sheath section 7, the needle tube 3, and the stylet 27 are deformed in a bent state. In this embodiment, a state in which the stylet 27 is inserted into the needle tube 3 is not essential. In the procedure of the biopsy on the pancreatic head as in this embodiment, the insertion body 2 is bent to an extent close to a performance limit of the active bending section 105 or the raising base 108 of the ultrasonic endoscope 100.

Next, the operator advances the needle slider 23 shown in FIG. 3 toward a distal end of the operation section 8. The sheath section 7 is set in the bent shape by the raising base 108, but the needle tip 5 is difficult to puncture the inner surface of the distal-end-side inner tube 74A. Thus, the needle tube 3 is pushed by the needle slider 23 toward the distal end of the sheath section 7.

When the distal end of the needle tube 3 slightly protrudes from the sheath section 7, the stylet 27 is returned into the needle tube 3. Thus, the needle tube 3 can puncture the tissue using the sharp needle tip 5 of the needle tube 3. After that, once the needle tube is drawn such that the distal end of the needle tube 3 is accommodated in the sheath section 7.

Next, as shown in FIG. 8, the operator further advances the needle slider 23 toward the distal end of the operation section 8 while the distal end of the sheath section 7 comes into contact with an intestinal wall. Thereby, the needle tip 5 of the needle tube 3 protrudes from the distal end of the sheath section 7, punctures the tissue, and is pushed toward the target tissue T on which the biopsy is performed. At this time, the stylet 27 is disposed near the distal end inside the needle tube 3 such that no tissue other than the biopsy target enters the needle tube 3. When tissue other than the biopsy target enters the needle tube 3, the stylet 27 protrudes from the distal end of the needle tube so that the tissue other than the biopsy target can be discharged from the needle tube.

The operator can acquire positional information of the distal-end-side portion of the needle tube 3 inserted into the tissue by the ultrasonic scanning mechanism 104. For this reason, the operator can observe an ultrasonic image indicating an image of the distal-end-side portion of the needle tube 3 acquired in the ultrasonic scanning mechanism 104 using the ultrasonic observation unit 115 shown in FIG. 1. The operator moves the distal end (the needle tip 5) of the needle tube 3 to the target tissue T on which the biopsy is performed while referencing to the image of the distal end portion of the needle tube 3 which is clearly displayed on the ultrasonic observation unit 115.

The operator pulls out the stylet 27 from the insertion body 2 and the operation section 8 to suction the tissue to the needle tube 3. Thus, a through hole which extends from the distal end of the needle tube 3 to the proximal end of the needle slider 23 is generated. The operator connects a syringe or the like to a port (not shown) arranged in the proximal end of the needle slider 23, suctions the needle tube 3, and collects cells or the like of the target tissue T on which the biopsy is performed by suctioning the needle tube 3 from the distal end of the needle tube 3. The needle tube may be finely moved in the target tissue T by advancing and retracting the needle slider 23 to acquire a greater amount of biopsy tissue.

When a necessary amount of cells or the like has been collected, the needle tube 3 is pulled out of the tissue by retracting the needle slider 23 toward a proximal end of the operation section 8, and the distal end of the needle tube 3 is accommodated in the sheath section 7. When the needle tube 3 has been pulled out of the tissue, the attachment adapter 18 is detached from the proximal end port 107*b* of the operation section 109 of the ultrasonic endoscope 100, and the puncture needle 1 is removed from the channel 107. Finally, the ultrasonic endoscope 100 is removed from the patient, and the series of treatments end.

Embodiments and examples of the present invention have been described in detail above with reference to the drawings, but a specific constitution is not limited to the embodiments, and various changes in design or the like are also included without departing from the gist of the present invention.

For example, in the above-described embodiments, in an entire length of the outer sheath, the distal-end-side inner tube may be arranged at only a region at which the outer sheath is assumed to be deformed in the bent shape by the raising base. In other words, the distal-end-side inner tube is arranged inside the outer sheath along the central line of the outer sheath in a range from the proximal end of the raising base to the distal end of the outer sheath. In this case, the distal end of the outer sheath is arranged at more distal position than the proximal end of the raising base when the attachment adapter 18 is attached to the endoscope 100. The distal end of the outer sheath may protrude from the channel 107.

In the above-described embodiments, in the entire length of the outer sheath, the distal-end-side inner tube may be arranged at only a region at which the outer sheath is assumed to be deformed in the bent shape by the raising base and the active bending section. In other words, the distal-end-side inner tube is arranged inside the outer sheath along the central line of the outer sheath in a range from the proximal end of the active bending section to the distal end of the outer sheath. In this case, the distal end of the outer sheath is arranged at more distal position than the proximal end of the active bending section when the attachment adapter 18 is attached to the endoscope 100.

In the above-described embodiments, when the ultrasonic endoscope does not have the raising base, in the entire length of the outer sheath, the distal-end-side inner tube may be arranged at only a region at which the outer sheath is assumed to be deformed in the bent shape by the active bending section. In other words, in this state, the distal-endside inner tube is arranged inside the outer sheath along the central line of the outer sheath in a range from the proximal end of the active bending section to the distal end of the outer sheath.

The ultrasonic endoscope may have a pipeline-shaped slope section which is inclined with respect to the central axis of the channel 107 in place of the raising base. In this case, the distal end of the outer sheath is arranged at more distal position than a proximal end of the slope section when the attachment adapter 18 is attached to the endoscope 100. In this state, in the entire length of the outer sheath, the distal-end-side inner tube may be arranged at only a region at which the outer sheath is assumed to be deviated by the slope section or a range including this region. In other words, in this state, the distal-end-side inner tube is arranged inside the outer sheath along the central line of the outer sheath in a range from the proximal end of the slope section to the distal end of the outer sheath.

Although embodiments of the present invention have been described, the technical scope of the present invention is not limited to these embodiments. The combinations of the components in the embodiments can be changed without departing from the gist of the present invention, or each component can be variously modified or removed. The present invention is not limited by the above description.

What is claimed is:

1. An endoscope puncture needle comprising:
    an outer sheath which is insertable into a channel of an endoscope;
    a needle tube having a needle tip, the needle tube being arranged inside the outer sheath;
    an operation main body connected to a proximal end of the outer sheath;
    a needle slider which is connected to a proximal end of the needle tube and which is movable along a longitudinal axis of the operation main body with respect to the operation main body;
    an engaging mechanism which has a contact surface that is formed on the needle slider and an engaging surface that is formed on the operation main body;
    a proximal-end-side inner tube which is arranged at an inside of a proximal end of the outer sheath and which is made of plastics; and
    a distal-end-side inner tube which is arranged at an inside of a distal end section of the outer sheath, through which the needle tube is insertable, and which is made of plastics, the distal-end-side inner tube having an inner circumferential surface that is relatively harder than the proximal-end-side inner tube,
    wherein the contact surface comes into contact with the engaging surface, and the needle slider is engaged to the operation main body in a longitudinal axial direction of the operation main body, and
    a distal end of the needle tube is arranged inside the distal-end-side inner tube when the needle slider is engaged to the operation main body.

2. The endoscope puncture needle according to claim 1, further comprising an attachment adapter which slidably supports the operation main body and which is attachable to the endoscope,
    wherein a distal end of the outer sheath is arranged at a more distal position than a proximal end of an active bending section when the attachment adapter is attached to the endoscope, the active bending section deforming the channel to a bent shape, and
    the distal-end-side inner tube is arranged inside the outer sheath along a central line of the outer sheath in a range from the proximal end of the active bending section to the distal end of the outer sheath.

3. The endoscope puncture needle according to claim 1, further comprising an attachment adapter which slidably supports the operation main body and which is attachable to the endoscope,
    wherein a distal end of the outer sheath is arranged at a more distal position than a proximal end of a raising base of the endoscope when the attachment adapter is attached to the endoscope, and
    the distal-end-side inner tube is arranged inside the outer sheath along a central line of the outer sheath in a range from the proximal end of the raising base to the distal end of the outer sheath.

4. The endoscope puncture needle according to claim 1, further comprising an attachment adapter which slidably supports the operation main body and which is attachable to the endoscope,
    wherein a distal end of the outer sheath is arranged at a more distal position than a proximal end of a pipeline-shaped slope section when the attachment adapter is attached to the endoscope,
    the pipeline-shaped slope section is inclined with respect to a central axis of the channel of the endoscope, and
    the distal-end-side inner tube is arranged inside the outer sheath along a central line of the outer sheath in a range from the proximal end of the pipeline-shaped slope section to the distal end of the outer sheath.

5. The endoscope puncture needle according to claim 1, further comprising an attachment adapter which slidably supports the operation main body and which is attachable to the endoscope,
    wherein when the attachment adapter is attached to the endoscope:
        a distal end of the outer sheath is located at a more distal position than a proximal end of a raising base of the endoscope, and
        a proximal end of the distal-end-side inner tube is located at a more proximal position of the outer sheath than the proximal end of the raising base, and
        a distal end of the proximal-end-side inner tube is located inside the outer sheath which is bent by an active bending section of the endoscope.

6. The endoscope puncture needle according to claim 1, wherein Shore hardness of an inner surface of the distal-end-side inner tube is higher than Shore hardness of an inner surface of the proximal-end-side inner tube.

7. A biopsy system comprising:
    an endoscope provided with a channel through which a treatment tool is capable of being inserted and a bending application section by which the treatment tool in the channel is bent; and
    an endoscope puncture needle being attachable to the endoscope, the endoscope puncture needle including:
        an outer sheath being insertable into a channel of an endoscope;
        a needle tube having a needle tip, the needle tube being arranged inside the outer sheath;
        an operation main body being connected to a proximal end of the outer sheath;
        a needle slider which is connected to a proximal end of the needle tube and which is movable along a longitudinal axis of the operation main body with respect to the operation main body;
        an engaging mechanism which has a contact surface that is formed on the needle slider and an engaging surface that is formed on the operation main body;

a proximal-end-side inner tube which is arranged at an inside of a proximal end section of the outer sheath and which is made of plastics; and a distal-end-side inner tube which is arranged at an inside of a distal end section of the outer sheath, through which the needle tube is insertable, and which is made of plastics, the distal-end-side inner tube having an inner circumferential surface that is relatively harder than the proximal-end-side inner tube, wherein the contact surface comes into contact with the engaging surface, and the needle slider is engaged to the operation main body in a longitudinal axial direction of the operation main body, and a distal end of the needle tube is arranged inside the distal-end-side inner tube when the needle slider is engaged to the operation main body.

8. An endoscope puncture needle comprising:

a sheath which is insertable into a channel of an endoscope;

a needle tube having a needle tip, the needle tube being arranged inside the sheath;

an operation main body connected to a proximal end of the sheath;

a needle slider which is connected to a proximal end of the needle tube and which is movable along a longitudinal axis of the operation main body with respect to the operation main body; and an engaging mechanism which has a contact surface that is formed on the needle slider and an engaging surface that is formed on the operation main body, the contact surface coming into contact with the engaging surface, and the needle slider being engaged to the operation main body in a longitudinal axial direction of the operation main body, wherein the sheath has:

a distal end region located at a more distal position than a position of the needle tip positioned inside the sheath in a state that the needle slider is engaged to the operation main body, and a proximal end region located at a more proximal position than a position of the needle tip in a state that the needle slider is engaged to the operation main body, and an inner circumferential surface of the distal end region is relatively harder than an inner circumferential surface of the proximal end region.

* * * * *